United States Patent
Claereboudt et al.

(10) Patent No.: US 8,541,762 B2
(45) Date of Patent: Sep. 24, 2013

(54) CHARGED PARTICLE IRRADIATION DEVICE AND METHOD

(75) Inventors: Yves Claereboudt, Corbais (BE); Gregory Saive, Liege (BE)

(73) Assignee: Ion Beam Applications SA, Louvain-la-Neuve (BE)

( * ) Notice: Subject to any disclaimer, the term of this patent is extended or adjusted under 35 U.S.C. 154(b) by 0 days.

(21) Appl. No.: 13/637,096

(22) PCT Filed: Mar. 30, 2011

(86) PCT No.: PCT/EP2011/054940
§ 371 (c)(1),
(2), (4) Date: Sep. 25, 2012

(87) PCT Pub. No.: WO2011/121037
PCT Pub. Date: Oct. 6, 2011

(65) Prior Publication Data
US 2013/0026388 A1 Jan. 31, 2013

(30) Foreign Application Priority Data
Mar. 31, 2010 (EP) ..................... 10158873

(51) Int. Cl.
*A61N 5/00* (2006.01)
(52) U.S. Cl.
CPC ....................... *A61N 5/00* (2013.01)
USPC .......................... 250/492.3; 378/65
(58) Field of Classification Search
USPC .......................... 250/492.3; 378/65
See application file for complete search history.

(56) References Cited

U.S. PATENT DOCUMENTS

| | | | |
|---|---|---|---|
| 6,600,164 B1 | 7/2003 | Badura | |
| 6,677,597 B1 | 1/2004 | Haberer | |
| 7,482,606 B2 * | 1/2009 | Groezinger et al. | 250/492.3 |
| 2011/0303857 A1 * | 12/2011 | Bert et al. | 250/492.1 |

\* cited by examiner

*Primary Examiner* — Kiet T Nguyen
(74) *Attorney, Agent, or Firm* — Christopher Casieri

(57) ABSTRACT

A charged particle irradiation device (10) and method for irradiating a target volume (50), adapted for receiving a treatment plan (70) defining a series of prescribed irradiation points (140) having each a prescribed dose to be delivered is provided. The device includes an irradiation unit (40) having at least one scanning magnet (100; 110), and at least one beam position monitor (130) installed in between the said scanning magnet (100; 110) and said target volume (50) is provided. A controller (80) comprises means for calculating for any said prescribed irradiation point corresponding nominal magnetic settings of the scanning magnet such that a beam (90) is pointing to said prescribed irradiation point when corresponding magnetic settings are applied, and means for calculating corresponding expected position at said beam position monitor (130) according to said first correction.

16 Claims, 2 Drawing Sheets

CHARGED PARTICLE IRRADIATION DEVICE AND METHOD

This application is a 371 application of PCT/EP2011/054940, filed Mar. 30, 2011, which, in turn, claims priority of European Patent Application No.: 10158873.9, filed on Mar. 31, 2010.

TECHNICAL FIELD

The invention relates to the field of charged particle irradiation devices and methods and more particularly to a device and a method for tuning the delivery of a charged particle beam (90).

DESCRIPTION OF RELATED ART

Radiotherapy using particles has proven to be a precise and conformal radiation therapy technique where a high dose to a target volume can be delivered while minimizing the dose to surrounding healthy tissues. A charged particle irradiation device comprises an accelerator producing an energetic charged particles beam, a beam transport line and an irradiation unit. The irradiation unit is responsible to deliver a conformal dose distribution to the target volume and monitor and measure the dose delivered. Various types of irradiation units exist, applying different techniques to deliver a conformal dose to the target volume. There are two major techniques used in particle beam delivery: the more common passive scattering techniques and the more sophisticated dynamic irradiation techniques.

An example of a dynamic technique is the so-called pencil beam scanning (PBS) technique. In PBS a narrow particle pencil beam is magnetically scanned on the plane orthogonal to the central beam direction. Lateral conformity in the target volume is obtained by adequate control of scanning magnets. By varying the energy of the particle beam, different layers in the target volume, characterized by their fixed particle energy, can subsequently be irradiated. In this way, particle radiation dose can be delivered to the entire 3D target volume.

The sum of all layer irradiations delivered to the target volume, while keeping the same beam-to-object geometry, is called a treatment beam or a treatment field. When using a charged particle irradiation device comprising a gantry device, various treatment beams can be delivered to the target volume from different gantry angles. Alternatively, the beam-to-object geometry can also be modified by rotations of the object with respect to the beam. The sum of all treatment beams to be delivered during the same irradiation session is defining a treatment fraction. The geometry and characteristics of the treatment beams to be delivered by the charged particle irradiation device during a fraction are specified in a treatment plan. Prior to irradiation the charged particle irradiation device receives a treatment plan from the treatment planning system, specifying the characteristics of the treatment beams to be delivered. The charged particle irradiation device is configurable for delivery of treatment beams based on a given set of treatment beam parameters specified in the treatment plan.

Multiple variations of pencil beam scanning techniques exist. There is the so-called spot scanning technique where the layer irradiation is performed by delivering a prescribed particle dose at discrete spot positions in the target volume and by interrupting the beam in-between spot positions. Another method is the continuous scanning technique where the beam spot is continuously scanned following a predefined scanning pattern. During the scanning of a layer, the particle intensity can be varied instant by instant in order to deliver the right particle radiation dose at the right place in the target volume, as specified in the treatment plan. In more advanced beam delivery systems also the scanning speed can be adjusted instant by instant in order to have an additional degree of freedom to modulate the particle intensity. Other variations of scanning techniques have been proposed. For example a scanning technique where at each spot position the particle energy is varied to cover the target region in depth before going to the next spot position. An even more advanced technique is a technique where both spot position and particle energy are varied together.

With the PBS technique, not only homogenous dose distributions can be delivered to the target volume but also inhomogeneous dose distributions can be delivered as specified with advanced treatment planning systems. Typically, a combination of several treatment beams coming from different beam directions (e.g. by selecting another gantry angle or by rotating the object with respect to the beam direction) is needed to produce a custom tailored radiation dose that maximizes the dose in the target volume while also protecting adjacent normal tissues. As a result, the 3-D dose distribution in the target volume resulting from one single treatment beam direction might not be uniform. It is uniform when the integral of the dose contributions from all treatment beams of the treatment fraction are delivered. The delivery of inhomogeneous treatment beams which add up to a homogenous and conformal dose in the target volume is called Intensity Modulated Particle Therapy (IMPT). The specification of the treatment beams is performed by advanced treatment planning systems using optimization algorithms to specify the number and directions of treatment beams and the particle intensities to be delivered for each spot position in each layer of each treatment beam.

Another example of a dynamic particle radiation technique that differs from pencil beam scanning is the so called wobbling technique, also named uniform scanning technique, where a uniform dose is delivered to a target volume layer per layer and the beam is continuously scanned over a fixed geometrical scanning pattern. In this method the beam does not follow the contour of the target volume but the beam is scanned within a predefined geometrical area (square, rectangle, circle, . . . ) and lateral conformity is accomplished by using a multileaf collimator or a patient specific aperture.

In order to deliver a charged particle beam with the highest accuracy, the dose and the position of the beam produced by the charged particle irradiation device is periodically calibrated using a water phantom. A water phantom is a standard calibration instrument. Usually, it is a water filled tank comprising a moveable ionization chamber or semi-conductor detector.

Also, in order to deliver a charged particle beam with the highest accuracy, monitoring means as e.g. ionization chambers, pixels chambers or stripped chambers, for on-line monitoring of the dose and the position of the beam, are comprised in the irradiation unit and/or in the beam transport line upstream the irradiation unit and/or on the patient couch between the patient and the irradiation unit.

It is of particular importance to avoid the misalignment of the beam. Causes of misalignment of the beam are discussed in publication "Engineering design and study of the beam position accuracy in the "Riesenrad" ion gantry", S. A. Reimoster, M. Pavlovic, in Nuclear Instruments and methods in Physics Research A 456 52001) 390-410. Misalignment of the beam can be caused by systematic errors and/or random errors. Common systematic errors are caused by elastic deformation of the gantry which is a cumbersome and weighting structure. Other systematic errors on the beam alignment can be caused e.g. by manufacturing errors or by initial alignment of the scanning magnets. Random errors are often caused by temperature effects or by non-reproducible alignments changes of individual beam transport elements during a rotation of the gantry. In this reference, the authors only suggest to stop the delivery of the beam if a monitoring means detects a wrong position of the beam, and then to correct the beam position by adjusting the setting of scanning magnets.

Document U.S. Pat. No. 6,677,597 discloses a method for the feedback control of a grid scanner ion beam therapy wherein the grid scanner has:

beam scanning magnets for directing the ion beam horizontally and vertically with respect to the middle of the beam, the scanning magnets being controlled by control and read-out modules;

monitoring means for beam location measurements;

a sequence control device which controls the activation and read-out sequence among the devices of the apparatus, wherein the method comprises the following steps:

comparison of the position, measured by said monitoring means, of the beam irradiating a first spot, with the desired position of said first spot;

determination of a correction value to supply to the scanning magnets according to the performed comparison;

setting the correction value to the scanner magnets for the realignment of the beam position for said first spot;

repeating the above steps for other spots to be irradiated.

In this method, the probability to have a discrepancy in the position of the beam for the irradiation of the first spot with respect to the desired beam position is high. Moreover, the authors describe in FIG. 3a a diagram of 49 beam positions and a method of irradiation starting from the top left hand corner of this diagram, thus an irradiation method starting at an extremity of the tumour. Since there is a high probability that the beam is incorrectly positioned for irradiating the first spot, the probability to irradiate healthy tissue is high. Also, in this irradiation method, the beam realignment is carried out from beam position to beam position and is thus time consuming. This device requires fast electronics for determining the correction value for each spot.

Other documents EP2005993 and EP1348465 disclose the monitoring of the direction taken by the beam using monitoring means, followed by the correction of the beam trajectory by computing correction values to set to the scanning or steering magnets and setting the scanning or steering magnets according to the correction values.

The above mentioned techniques presents some drawbacks. For the treatment of a tumour with the pencil beam scanning technique or spot scanning technique, the probability to have systematic or random errors in the alignment of the beam is high, and in this case, irradiation of a first small volume element comprised in a target volume, i.e. the tumour, will not start at the suited targeted volume element but at another volume element which could be a part of healthy tissue. For irradiating a tumour or a layer of the tumour by f.i. continuous scanning, if the beam irradiates a first volume element at a wrong position, errors will be made for the next elements volumes to be irradiated. Also, as explained in the above referenced publication of Reismoster et al., misalignment of the beam with respect to a target volume element can occur after the rotation of the gantry. Since a good alignment and setting of the scanning magnets is important for guaranteeing an accurate treatment, there is a need for a charged particle irradiation device and a method able to scan a tumour by a charged particle beam in an accurate way starting from a well defined first target volume element comprised in a target volume (i.e. a tumour) in accordance to the treatment plan and thus minimizing errors of delivery on the defined first and further volume elements comprised in the tumour. The method has to be efficient and fast in order to allow the treatment of a large number of patients limiting the need of a time consuming calibration using a water phantom.

SUMMARY OF THE INVENTION

According to a first aspect, the invention relates to a charged particle irradiation device for irradiating a target volume, adapted for receiving a treatment plan defining a series of prescribed irradiation points having each a prescribed dose to be delivered, comprising an accelerator, a beam transport system and an irradiation unit having at least one scanning magnet, a dose detector and at least one beam position monitor installed in between the said scanning magnet and said target volume, a controller comprising means for calculating for any said prescribed irradiation point corresponding nominal magnetic settings of the scanning magnet such that the beam is pointing to said prescribed irradiation point when corresponding magnetic settings are applied and means for calculating a corresponding expected position at said beam position monitor.

According to the invention, the controller further comprises:

a) means for selecting a tuning reference point from said series of prescribed irradiation points;

b) means for specifying a prescribed tuning dose to be given to said selected tuning reference point, said prescribed tuning dose being equal or smaller than the said prescribed dose at said selected tuning reference point;

c) means for comparing a beam position provided by the beam position monitor and the expected position at said beam position monitor for said selected tuning reference point;

d) means for computing a first correction to be applied to said nominal magnetic settings of the scanning magnet in order to align the beam position provided by the beam position monitor to the expected position at said beam position monitor for said selected tuning reference point;

e) means for correcting the nominal magnetic settings of the scanning magnet for all said prescribed irradiation points according to said first correction.

Hence, a device according to the invention only needs to perform one single measurement of the beam position at one reference point in order to be able to determine the corrections to be applied to the magnetic settings of the scanning magnet for all prescribed irradiation points.

The means for selecting a tuning reference point are preferably adapted to select a tuning reference point either among the irradiation points with the highest prescribed dose, or in the centre of a convex area of irradiation points having a prescribed dose above a threshold, or at random in a convex area of irradiation points having a prescribed dose above a threshold.

Preferably, the means for specifying a prescribed tuning dose are adapted to specify a prescribed tuning dose smaller than one tenth, preferably smaller than hundredth of the prescribed dose for the selected tuning reference point.

More preferably, said controller further comprises means for subtracting said prescribed tuning dose from the prescribed dose for said selected tuning reference point or for the nearest irradiation point.

According to a second aspect, the invention relates to a method for tuning the delivery of a charged particle beam in a charged particle irradiation device for irradiating a target volume, adapted for receiving a treatment plan defining a series of prescribed irradiation points having each a prescribed dose to be delivered, comprising an accelerator, a beam transport system and an irradiation unit having at least one scanning magnet, a dose detector and at least one beam position monitor installed in between the said scanning magnet and said target volume, a controller comprising means for calculating for any said prescribed irradiation point corresponding nominal magnetic settings of the scanning magnet such that the beam is pointing to said prescribed irradiation point when corresponding magnetic settings are applied and means for calculating a corresponding expected position at said beam position monitor.

According to the invention, the method comprises the steps of:
a) selecting a tuning reference point from said series of prescribed irradiation points;
b) specifying a prescribed tuning dose to be given to said selected tuning reference point, said prescribed tuning dose being equal or smaller than the said prescribed dose at said selected tuning reference point;
c) comparing a beam position provided by the beam position monitor and the expected position at said beam position monitor for said selected tuning reference point;
d) computing a first correction to be applied to said nominal magnetic settings of the scanning magnet in order to align the beam position provided by the beam position monitor to the expected position at said beam position monitor for said selected tuning reference point;
e) correcting the nominal magnetic settings of the scanning magnet for all said prescribed irradiation points according to said first correction.

The step of selecting a tuning reference point may select a tuning reference point among the irradiation points with the highest prescribed dose, or in the centre of an area of irradiation points having a prescribed dose above a threshold, or even at random in an area of irradiation points having a prescribed dose above a threshold.

Preferably, the step of specifying a prescribed tuning dose specifies a prescribed tuning dose smaller than one hundredth of the prescribed dose for the selected tuning reference point or for the nearest irradiation point.

The method may further comprise the step of subtracting said prescribed tuning dose from the prescribed dose for said selected tuning reference point.

DETAILED DESCRIPTION OF EMBODIMENTS OF THE INVENTION

Figure 1:
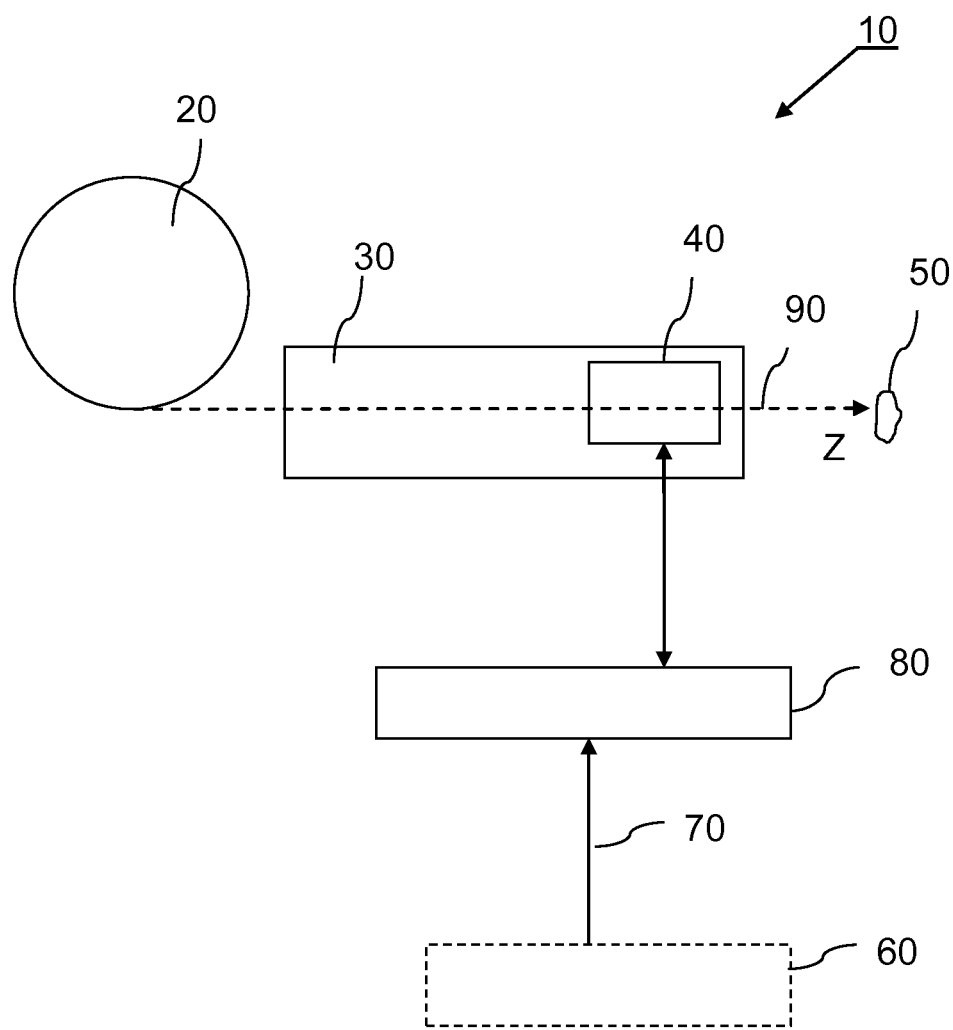
FIG. 1 is a schematic view of an exemplary charged particle irradiation device according to the invention.

FIG. 1 is a general schematic of an exemplary charged particle irradiation device 10 according to the invention. It comprises an accelerator 20 which may for example be a cyclotron or a synchrotron for accelerating charged particles such as for example protons, alpha particles or carbon ions. A beam transport line 30 transports the beam of charged particles 90 up to a location where a target 50 is located. The target 50 may either be a phantom for measuring the beam or a (part of a) patient to be treated. An irradiation unit 40 performs the function of shaping or directing the beam according to the requirements of the treatment plan. A controller 80 performs the function of, among others, controlling the irradiation unit 40. A treatment planning system 60 (not part of the charged particle irradiation device 10, but shown on FIG. 1 for clarity) provides a treatment plan 70 to the controller 80. In the case of a pencil beam scanning (PBS) technique, the treatment plan comprises a set of prescribed irradiation points, associated with prescribed doses to be delivered respectively at said points. The irradiation points are usually associated as "layers", each layer being located at a given depth in the target.

Figure 2:
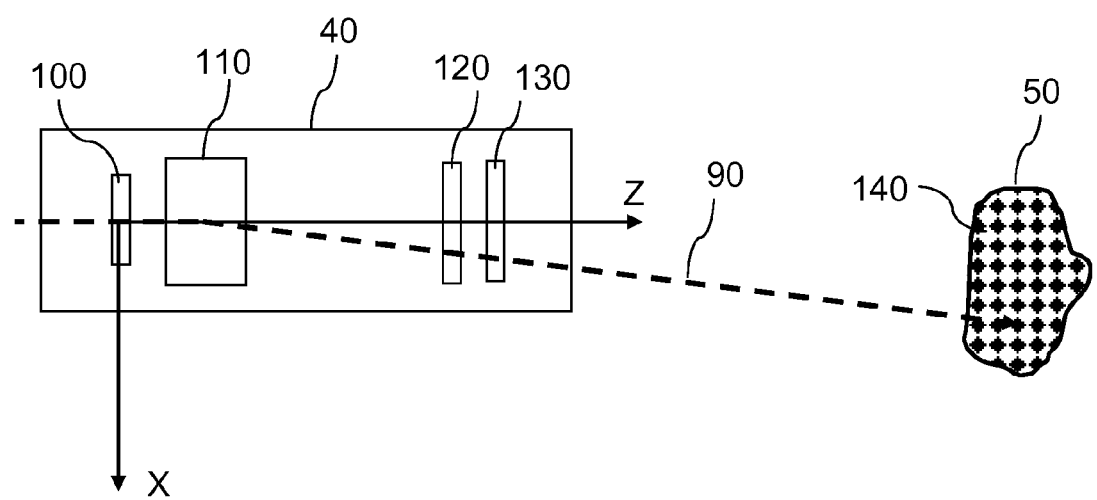
FIG. 2 is a more detailed view of an irradiation unit for use in the invention.

FIG. 2 is a more detailed view of an irradiation unit 40 for use in the invention. The irradiation unit 40 comprises a first scanning magnet 100 for deviating the beam 90 in a first direction (X) perpendicular to a main beam axis (Z) and a second scanning magnet 110 for deviating the beam 90 in a second direction (Y) also perpendicular to the main beam axis (Z) and to the first direction (X). In addition, a beam position monitor 130 is provided for measuring an (X,Y) position of the beam. The beam position monitor 130 may for example be a set of wire counters disposed perpendicularly, or an XY matrix of ionisation chambers. The irradiation unit 40 may optionally also comprise a dose detector 120. This dose detector 120 may for example be a full plane ionisation chamber. The dose detector measures the dose delivered to the target 50 by the beam 90 traversing it.

According to the invention, the controller 80 performs the following functions:
a) after receiving a treatment plan 70 from the treatment planning system 60, selecting a tuning reference point from the received series of prescribed irradiation points 140;
b) specifying a prescribed tuning dose to be given to said selected tuning reference point, said prescribed tuning dose being equal or smaller than the prescribed dose at said selected tuning reference point; the tuning reference point is then irradiated with the beam until it has received the prescribed tuning dose;
c) in the course of the irradiation of the tuning reference point with the prescribed tuning dose, comparing a beam position provided by the beam position monitor 130) and the expected position at said beam position monitor 130 for said selected tuning reference point;
d) computing a first correction to be applied to said nominal magnetic settings of the scanning magnets (100; 110) in order to align the beam position provided by the beam position monitor 130 to the expected position at said beam position monitor 130 for said selected tuning reference point; this first correction may be a simple linear correction of the magnet currents. The parameters giving the magnet current correction in function of the position deviation are preferably determined beforehand by a measurement or a computation;
e) correcting the nominal magnetic settings of the scanning magnet for all said prescribed irradiation points according to said first correction.

For performing the function e), the controller 80 may for example first compute the corrections to be applied to the nominal magnetic settings of the scanning magnets for each prescribed irradiation point, each correction being a function of said first correction, and then compute and store corrected magnetic settings of the scanning magnet for each prescribed irradiation point on the basis of the computed corrections, and then control the scanning magnets according to the corrected magnetic settings when scanning the beam over the target.

Alternatively, the controller may compute and apply these corrections irradiation point by irradiation point in the course of the scanning irradiation process.

The corrections applied to the nominal magnetic settings of the scanning magnets for each prescribed irradiation point may for example all be the same function of the first correction:

correction for point "1"=correction for point "2"= . . . =correction for point "$n$"=$f$(first correction)

In a particular case, the correction for each prescribed irradiation point is equal to the first correction.

Alternatively, the corrections to be applied to the nominal magnetic settings of the scanning magnet for each prescribed irradiation point may be a different function of the first correction:

correction for point "1" = $f1$(first correction), correction for point "2" = $f2$(first correction),

...

correction for point "$n$" = $fn$(first correction), wherein f1, f2, . . . , fn are functions among which at least two functions are different from each other.

It must of course be understood that any correction comprises in fact two correction values: one value for the first scanning magnet 100 ("X" correction) and another value for the second scanning magnet 110 ("Y" correction).

In another particular case, the correction for a given irradiation point is a function of the first correction and of the X,Y position of that irradiation point:

"X" correction for point "$i$"=$f(Xi$, first correction_X),

"Y" correction for point "$i$"=$f(Yi$, first correction_Y), wherein Xi,Yi are respectively the X,Y coordinates of point "i" and wherein "first correction_X" is the first correction for the first scanning magnet 100 and "first correction_Y" is the first correction for the second scanning magnet 110.

The functionalities performed in steps c), d) and e) by the controller 80 will now be further detailed with an exemplary calculation.

The position of a beam at the level of the beam position monitor 130 is identified by coordinates (XMonitor, YMonitor) in a beam position monitor referential and the position of the same beam at the level of the so-called isocenter where the target 50 is located is identified by coordinates (Xisoc, Yisoc) in an isocenter referential. The beam position monitor referential and the isocenter referential are both perpendicular to the main beam axis (Z). The isocenter referential has its origin on the main beam axis (Z).

When considering a beam that is unscanned (i.e. both scanning magnets 100 and 110 are off), a set of four parameters ($\alpha x$, $\beta x$, $\alpha y$, $\beta y$) define a correlation between the position of this unscanned beam at the beam position monitor 130 and its position at isocenter through the following equations:

$X$isoc=$\alpha x$*$X$Monitor+$\beta x$ $Y$isoc=$\alpha y$*$Y$Monitor+$\beta y$

These equations are linking the coordinates systems at the level of the isocenter plane and at the level of the beam position monitor 130.

The theoretical position of an unscanned beam at the isocenter plane is defined through coordinates (IsoXUnscan, IsoYUnscan) in the isocenter referential and the corresponding coordinates in the beam position monitor referential can be calculated with the above equations.

These positions at isocenter of an unscanned beam need to be taken into account for calculating the deflections to be applied by the scanning magnets 100, 110 in order to bring the beam to a given irradiation point.

Indeed, consider the position coordinates (DeflX, DeflY) as the expected position of the beam in the isocenter referential for one of the irradiation positions 140. Then the total deflection (dX, dY) to be applied by the scanning magnets 100, 110 to reach the expected position (DeflX, DeflY) is computed through:

$dX$=Defl$X$+Iso$X$Offset $dY$=Defl$Y$+Iso$Y$Offset, wherein

Iso$X$Offset=−Iso$X$Unscan

Iso$Y$Offset=−Iso$Y$Unscan

Corresponding to these deflections (dX,dY), a position at the beam position monitor (XMonitor, YMonitor) can now be computed through the relations:

$X$Monitor=($dX$*Distanceto$X$Magnet/$SADX$)+(Iso$X$Unscan−$\beta x$)/$\alpha x$ $Y$Monitor=($dY$*Distanceto$Y$Magnet/$SADY$)+(Iso$Y$Unscan−$\beta y$)/$\alpha y$, wherein SADX and SADY are the source to axis distance in X and Y respectively and DistancetoXMagnet and DistancetoYmagnet are the distances from the beam position monitor to the respective scanning magnets.

When calculating magnetic settings of the scanning magnets for the irradiation points, the problem is that the values of IsoXoffset and IsoYoffset are not well known as they can vary and hence corrections need to be applied.

The device and method of the invention provides for correcting the nominal magnetic deflections (i.e. magnetic settings of the scanning magnets) for all irradiation points according to a first correction corresponding to an IsoOffset correction that is determined by performing a measurement at a tuning reference point.

When making an irradiation at the tuning reference point as discussed above, one compares the beam position provided by the beam position monitor 130 (i.e. the measured position: XMeasured and YMeasured) with the expected position at the beam position monitor (XExpected and YExpected) as follows (i.e. to perform function c) of the controller discussed above):

Delta$X$Monitor=$X$Expected−$X$Measured

Delta$Y$Monitor=$Y$Expected−$Y$Measured

These comparisons are then linked with a position error (XErrorIso, YErrorIso) at isocenter through the following relation:

$X$ErrorIso=$\alpha x$.Delta$X$Monitor $Y$ErrorIso=$\alpha y$.Delta$Y$Monitor

These errors correspond to a first correction that needs to be applied to the scanning magnets in order to bring the beam from the measured to the expected position at the tuning reference point (i.e. to perform function d) of the controller discussed above).

In a further step (function e)) of the controller discussed above), corrections to the deflections of the scanning magnets (i.e. corrections to the magnetic settings of said magnets) for all the prescribed irradiation points are made according to the first correction. For calculating the deflections for all irradiations points, a new IsoOffset in X and Y is first calculated as follows:

$$XNewIsoOffset = -IsoXUnscan + XErrorIso$$

$$YNewIsoOffset = -IsoYUnscan + YErrorIso$$

The total scanning magnet deflections (DX,DY) for an irradiation point having expected positions (DeflX,DeflY) in the isocenter referential are then expressed as follows:

$$DX = DeflX + XNewIsoOffset$$

$$DY = DeflY + YNewIsoOffset$$

The same equation is used for calculating the new total magnetic deflections (DX,DY), i.e. magnetic settings to be applied to the scanning magnets, for all irradiation points 140 having expected positions (DeflX,DeflY) in the isocenter referential.

This exemplary calculation method is based on the assumption that the deflections induced by the scanning magnets are reproducible and independent from the incoming beam.

The selection of the tuning reference point is preferably made in order to reduce the risk of irradiating healthy tissue. To this end, the tuning reference point is preferably selected either among the irradiation points with the highest prescribed dose, or in the centre of a convex area of irradiation points having a prescribed dose above a threshold, or at random in a convex area of irradiation points having a prescribed dose above a threshold.

Preferably, the tuning dose delivered during the tuning is subtracted either from the prescribed dose of the tuning reference point (for example when the misalignment is small), or from the prescribed dose of the nearest irradiation point (for example when the misalignment is more important).

Whatever the chosen location of the tuning reference point, the tuning dose is preferably selected as being small with regard to the prescribed dose of said tuning reference point, yet being sufficient for the beam position monitor 130 to perform a meaningful and precise measurement. Preferably, the tuning dose is less than one tenth, more preferably less than one hundredth of the prescribed dose for the tuning reference point.

By using the irradiation device and method of the invention, there is no need to insert a beam stop between the irradiation unit 40 and the target 50 during a tuning phase. The invention is particularly useful when using small spot sizes (such as spot size of a few millimeters diameter for example). Indeed, when using a small spot size, a small misalignment of the particle beam (a few millimeters) can cause the irradiation to be performed far from the prescribed irradiation point.

In the context of the present invention, it must be understood that "a series of prescribed irradiation points" must not necessarily strictly represent all points of the target to be irradiated, but may represent a part of the target. In case the "series of prescribed irradiation points" represent only a part of the target, such as a layer of the target or even a part of a layer of the target, there may be several "tuning reference points"—one for each part of the target—and hence several corresponding first corrections, without departing from the scope of the invention.

The present invention has been described in terms of specific embodiments, which are illustrative of the invention and not to be construed as limiting. More generally, it will be appreciated by persons skilled in the art that the present invention is not limited by what has been particularly shown and/or described hereinabove. The invention resides in each and every novel characteristic feature and each and every combination of characteristic features.

Reference numerals in the claims do not limit their protective scope.

Use of the verbs "to comprise", "to include", "to be composed of", or any other variant, as well as their respective conjugations, does not exclude the presence of elements other than those stated.

Use of the article "a", "an" or "the" preceding an element does not exclude the presence of a plurality of such elements.

The invention claimed is:

1. A charged particle irradiation device (10) for irradiating a target volume (50), adapted for receiving a treatment plan (70) defining a series of prescribed irradiation points (140) having each a prescribed dose to be delivered, comprising an accelerator (20), a beam transport system (30) and an irradiation unit (40) having at least one scanning magnet (100; 110), a dose detector (120) and at least one beam position monitor (130) installed in between said scanning magnet (100; 110) and said target volume (50), a controller (80) comprising means for calculating for any said prescribed irradiation point corresponding nominal magnetic settings of the scanning magnet such that a beam (90) is pointing to said prescribed irradiation point when corresponding magnetic settings are applied, and means for calculating a corresponding expected position at said beam position monitor (130), characterized in that said controller (80) further comprises:
   a) means for selecting a tuning reference point from said series of prescribed irradiation points;
   b) means for specifying a prescribed tuning dose to be given to said selected tuning reference point, said prescribed tuning dose being equal or smaller than said prescribed dose at said selected tuning reference point;
   c) means for comparing a beam position provided by the beam position monitor (130) and the expected position at said beam position monitor (130) for said selected tuning reference point;
   d) means for computing a first correction to be applied to said nominal magnetic settings of the scanning magnet (100; 110) in order to align the beam position provided by the beam position monitor to the expected position at said beam position monitor (130) for said selected tuning reference point;
   e) means for correcting the nominal magnetic settings of the scanning magnet for all said prescribed irradiation points according to said first correction.

2. The charged particle irradiation device (10) according to claim 1 wherein the means for selecting a tuning reference point are adapted to select a tuning reference point among the irradiation points (140) with the highest prescribed dose.

3. The charged particle irradiation device (10) according to claim 1 wherein the means for selecting a tuning reference point are adapted to select a tuning reference point in the center of a convex area of irradiation points (140) having a prescribed dose above a threshold.

4. The charged particle irradiation device (10) according to claim 1 wherein the means for selecting a tuning reference point are adapted to select a tuning reference point at random in a convex area of irradiation points (140) having a prescribed dose above a threshold.

5. The charged particle irradiation device (10) according to any of preceding claims wherein the means for specifying a prescribed tuning dose are adapted to specify a prescribed tuning dose smaller than one tenth of the prescribed dose for the selected tuning reference point.

6. The charged particle irradiation device (10) according to claim 5 wherein the means for specifying a prescribed tuning dose are adapted to specify a prescribed tuning dose smaller than one hundredth of the prescribed dose for the selected tuning reference point.

7. The charged particle irradiation device (10) according to claim 6 wherein said controller (80) further comprises means for subtracting said prescribed tuning dose from the prescribed dose for said selected tuning reference point or for the nearest irradiation point.

8. The charged particle irradiation device (10) according to claim 5 wherein said controller (80) further comprises means for subtracting said prescribed tuning dose from the prescribed dose for said selected tuning reference point or for the nearest irradiation point.

9. A method for tuning the delivery of a charged particle beam (90) in a charged particle irradiation device (10) for irradiating a target volume (50), adapted for receiving a treatment plan (70) defining a series of prescribed irradiation points (140) having each a prescribed dose to be delivered, comprising an accelerator (20), a beam transport system (30) and an irradiation unit (40) having at least one scanning magnet (100; 110), a dose detector (120) and at least one beam position monitor (130) installed in between said scanning magnet (100; 110) and said target volume (50), a controller (80) comprising means for calculating for any of said prescribed irradiation points (140) corresponding nominal magnetic settings of the scanning magnet (100; 110) such that the beam is pointing to said prescribed irradiation point (140) when corresponding magnetic settings are applied, and means for calculating an expected position at said beam position monitor, characterized in that it comprises the steps of:
  a) selecting a tuning reference point from said series of prescribed irradiation points (140);
  b) specifying a prescribed tuning dose to be given to said selected tuning reference point, said prescribed tuning dose being equal or smaller than said prescribed dose at said selected tuning reference point;
  c) comparing a beam position provided by the beam position monitor (130) and the expected position at said beam position monitor (130) for said selected tuning reference point;
  d) computing a first correction to be applied to said nominal magnetic settings of the scanning magnet (100; 110) in order to align the beam position provided by the beam position monitor (130) to the expected position at said beam position monitor (130) for said selected tuning reference point;
  e) correcting the nominal magnetic settings of the scanning magnet for all said prescribed irradiation points according to said first correction.

10. The method according to claim 9 wherein the step of selecting a tuning reference point selects a tuning reference point among the irradiation points (140) with the highest prescribed dose.

11. The method according to claim 9 wherein the step of selecting a tuning reference point selects a tuning reference point in the center of a convex area of irradiation points (140) having a prescribed dose above a threshold.

12. The method according to claim 9 wherein the step of selecting a tuning reference point selects a tuning reference point at random in a convex area of irradiation points (140) having a prescribed dose above a threshold.

13. The method according to any of claims 9 to 12 wherein the step of specifying a prescribed tuning dose specifies a prescribed tuning dose smaller than one tenth of the prescribed dose for the selected tuning reference point.

14. The method according to claim 13 wherein the step of specifying a prescribed tuning dose specifies a prescribed tuning dose smaller than one hundredth of the prescribed dose for the selected tuning reference point.

15. The method according to claim 14 further comprising the step of subtracting said prescribed tuning dose from the prescribed dose for said selected tuning reference point or for the nearest irradiation point.

16. The method according to claim 13 further comprising the step of subtracting said prescribed tuning dose from the prescribed dose for said selected tuning reference point or for the nearest irradiation point.

* * * * *